United States Patent [19]

Kirby

[11] Patent Number: 5,008,539

[45] Date of Patent: Apr. 16, 1991

[54] PROCESS AND APPARATUS FOR DETECTING PRESENCE OF PLANT SUBSTANCES

[75] Inventor: John A. Kirby, Las Vegas, Nev.

[73] Assignee: The United States of America as represented by the United States Department of Energy, Washington, D.C.

[21] Appl. No.: 561,633

[22] Filed: Aug. 1, 1990

[51] Int. Cl.$^5$ .................. G01N 33/00; G01T 1/20
[52] U.S. Cl. ................ 250/336.1; 250/358.1; 250/362
[58] Field of Search ............ 250/361 R, 362, 358.1, 250/336.1

[56] References Cited

U.S. PATENT DOCUMENTS

| | | | |
|---|---|---|---|
| 1,933,063 | 10/1933 | Kolhörster | 250/376 |
| 2,337,306 | 12/1943 | Barnes | 250/375 |
| 4,590,377 | 5/1986 | Lukens | 250/361 R |

*Primary Examiner*—Carolyn E. Fields
*Assistant Examiner*—Drew A. Dunn
*Attorney, Agent, or Firm*—Michael Lee; L. E. Carnahan; William R. Moser

[57] ABSTRACT

An apparatus and process for detecting the presence of plant substances in a particular environment which comprises the steps of: measuring the background K40 gamma ray radiation level in a particular environment with a 1.46 MeV gamma ray counter system; measuring the amount of K40 gamma ray radiation emanating from a package containing a plant substance being passed through an environment with a counter; and generating an alarm signal when the total K40 gamma ray radiation reaches a predetermined level over and above the background level.

17 Claims, 5 Drawing Sheets

PROCESS AND APPARATUS FOR DETECTING PRESENCE OF PLANT SUBSTANCES

FIELD OF THE INVENTION

The U.S. Government has rights to this invention pursuant to Contract No. W-7405-ENG-48 between the U.S. Department of Energy and the University of California, for the operation of Lawrence Livermore National Laboratory.

This invention is concerned with a process and apparatus for detecting the presence of plant substances in a particular environment. More particularly, it is concerned with a process of detecting the presence of plant substances using gamma ray scintillation detectors and counters to measure the level of potassium 40 gamma radiation being given off by substances.

BACKGROUND OF THE INVENTION

The possession of marijuana and other substances such as cocaine and heroin is illegal in most states of the United States of America. These substances, however, are often imported or smuggled into the United States from various foreign countries, or, in the case of marijuana, is indigenously grown, and transported from one state to another by various means, including through the use of common carriers such as trucks, buses and airplanes. There is, at present, no adequate means of detecting marijuana or other illegal substances in luggage or packages being transported by individuals. In airports in particular, luggage is often x-rayed prior to its being placed on an airplane. However, x-rays do not specifically pick up marijuana or other illegal substances; thus, it is often transported from state to state undetected.

What is needed is a simple and economical means of detecting plant substances and other illegal plant substances in luggage or other packages as it is passed through check points at customs, airports, bus lines, or other common carriers.

THE PRIOR ART

U.S. Pat. No. 4,288,344 is concerned with stable diazonium salt generators for improved plant substances analyses. In the process described, a quantity of plant substance (i.e., marijuana), is placed on white paper or cloth, then successively covered by one drop each of the diazotizing and developer reagents described. If the plant material is marijuana, coupling of the generated diazonium salt with plant phenols will produce a red dye.

U.S. Pat. No. 2,337,306 discloses a method for conducting quantitative analyses, which embraces the determination of the total quantity of an element present in a sample where that element is present in the form of its radioactive and non-radioactive isotopes. The patent states that the invention is predicated upon the discovery that naturally or artificially radioactive elements give off or emit radiations such as beta-rays or electrons, and gamma rays or x-rays of very short wave length, in an amount depending on the quantity of the occuring radioactive element present. The radioactivity of the elements is measured by means of a Geiger-Muller counter. In this patent, it is disclosed that a radioactive isotope of potassium is present naturally and uniformly as a small part, with ordinary potassium. This naturally radioactive isotope, known as K40, is stated to have an extremely long half-life, of the order of $1 \times 10^9$ years, thus any decay which takes place while the analysis for potassium is being conducted by the measurement of its radioactivity is safely neglected, being within the field of experimental error. The method is directed to the determination of the total quantity of elements, for example, potassium, present in a sample where the potassium occurs in the form of its radioactive and non-radioactive isotopes, and in the substantial absence of unknown, interfering radioactivity, which comprises measuring the radioactivity emitted from the isotope and apparatus calibrated by measuring the radioactivity of standard potassium solutions under similar conditions, applying to that measurement a decay factor and calculating therefrom the total quantity of potassium present.

U.S Pat. No. 1,933,063 relates to an apparatus for determining the potassium content in spaces which contain potassium compounds. The content of potassium is measured by means of gamma rays emitted by the potassium which is present in a device wherein the actual sample is present inside a glass bulb.

As seen from the foregoing, the prior art processes all require that samples of marijuana be isolated from their natural environment and subjected to various tests, all of which is impossible to do in an environment such as an airport lobby, where speed and convenience is of paramount importance.

It would be desirable, therefore, to provide in the art a method of detecting the presence of marijuana or other plant substances in luggage and other packages which is safe, simple, accurate, and economical, and which would not unduly burden the furtherance of commerce and travel.

SUMMARY OF THE INVENTION

Accordingly, an object of the invention is to provide a means of detecting the presence of marijuana or other plant substances in luggage or other packages without the necessity of opening the luggage or other packages.

Another object of the invention is to provide a simple and economical way of detecting the presence of marijuana or other plant substances in luggage and other packages using K40 emissions from the substance.

A further object of the invention is to provide apparatus for detecting the presence of marijuana or other plant substances in a particular environment.

It is known that naturally occurring radioisotopes of the uranium and thorium series and potassium 40 are present in nearly all materials in our environment in widely varying concentrations. These radionuclides can be readily detected and identified in-situ using gamma ray detectors whose pulse height output is proportional to the energy deposited in the detector. If an incoming gamma ray is completely absorbed in the detector, the resulting pulse height will be proportional to the energy of the incoming gamma ray. Many radionuclides have characteristic energy gamma emissions and can, therefore, be identified from the pulse height spectrum, assuming the energy resolution of the detector is sufficient to resolve closely spaced peaks. Potassium 40 (K40) emits a 1.46 MeV gamma ray during (on the average) 11 percent of its disintegrations, and ordinary potassium contains 0.0119 percent K40. This results in an activity of 820 picocuries (pCi) of K40 per gram of potassium and an average emission rate of 198.4 gamma rays per minute for every gram of potassium.

It is known that plants uptake potassium (from potash) as a required nutrient along with phosphorous and nitrogen. It is also known that this uptake results in a relatively high concentration of potassium in the plant, depending on the species and which part of the plant is considered, especially when the plant is dried. Typical concentrations are from 1 to 10 percent potassium by dried weight, resulting in K40 concentrations of 8.2 to 82 pCi of K40 per gram of plant material. A gamma count of samples of processed and unprocessed marijuana shows concentrations of from 30 to 55 pCi of K40 per gram and the absence of any other detectable gamma emitters. The plants apparently don't uptake comparable concentrations of the uranium or thorium isotopes because these elements are not chemically similar to their required nutrients.

The process of this invention is a means for detecting the presence of plant substances in a particular environment which comprises the steps of:

(a) measuring the background K40 gamma ray radiation level in a particular environment with a 1.46 MeV gamma ray radiation counter system;

(b) measuring the amount of K40 gamma ray radiation emanating from a package containing plant substances being passed through said environment with said counter; and (c) generating a warning signal when the total K40 gamma ray radiation reaches a predetermined level over and above the background level.

The apparatus forming a part of the invention is that apparatus including the configurations thereof necessary to detect and count the 1.46 MeV K40 gamma rays being emitted from a package containing a plant substance, and convert the gamma ray radiation values obtained into a warning signal when the values reach a predetermined level.

The predetermined level is a function of the desired statistical certainty of detection for a given amount of K40 (or marijuana) in the package.

The objects and advantages of the invention may be realized and obtained by means of the instrumentalities and process particularly pointed out in the drawings, the descriptions to follow, and appended claims.

DETAILED DESCRIPTION OF THE PREFERRED EMBODIMENT

Simply stated, the process used to detect the presence of marijuana or other illegal plant substance in luggage or similar size packages is to determine with appropriate equipment the count rate of 1.46 MeV gammas from the luggage; and, if that count rate is statistically higher than the predetermined background count rate, generating an alarm indicating that some amount of K40 in the luggage is causing the higher count rate. In addition, the count rate above background can be used to calculate the approximate amount of K40 (or marijuana) in the sample.

Assuming that the amount of K40 due to empty luggage and normally encountered contents is small compared to the amount of K40 present in a designed minimum detectable weight of illegal plant substance (because of the relatively high concentration of potassium in the plant substance, preferably marijuana), it can be stated that although a piece of luggage that triggers an alarm may not absolutely contain the illegal plant substance, the probabilities are significantly increased over a random selection that a physical selection inspection will be beneficial. In fact, it is more correct to say that the system will separate the luggage that does not contain the illegal plant substance above a known minimum amount (or an equivalent amount of K40) from the luggage which does contain a minimum detectable amount of K40. The sensitivity of the system can be enhanced by reducing the environmental gamma ray background through shielding, low background material selection, and selection of detectors that are most efficient at 1.46 MeV.

Figure 1:
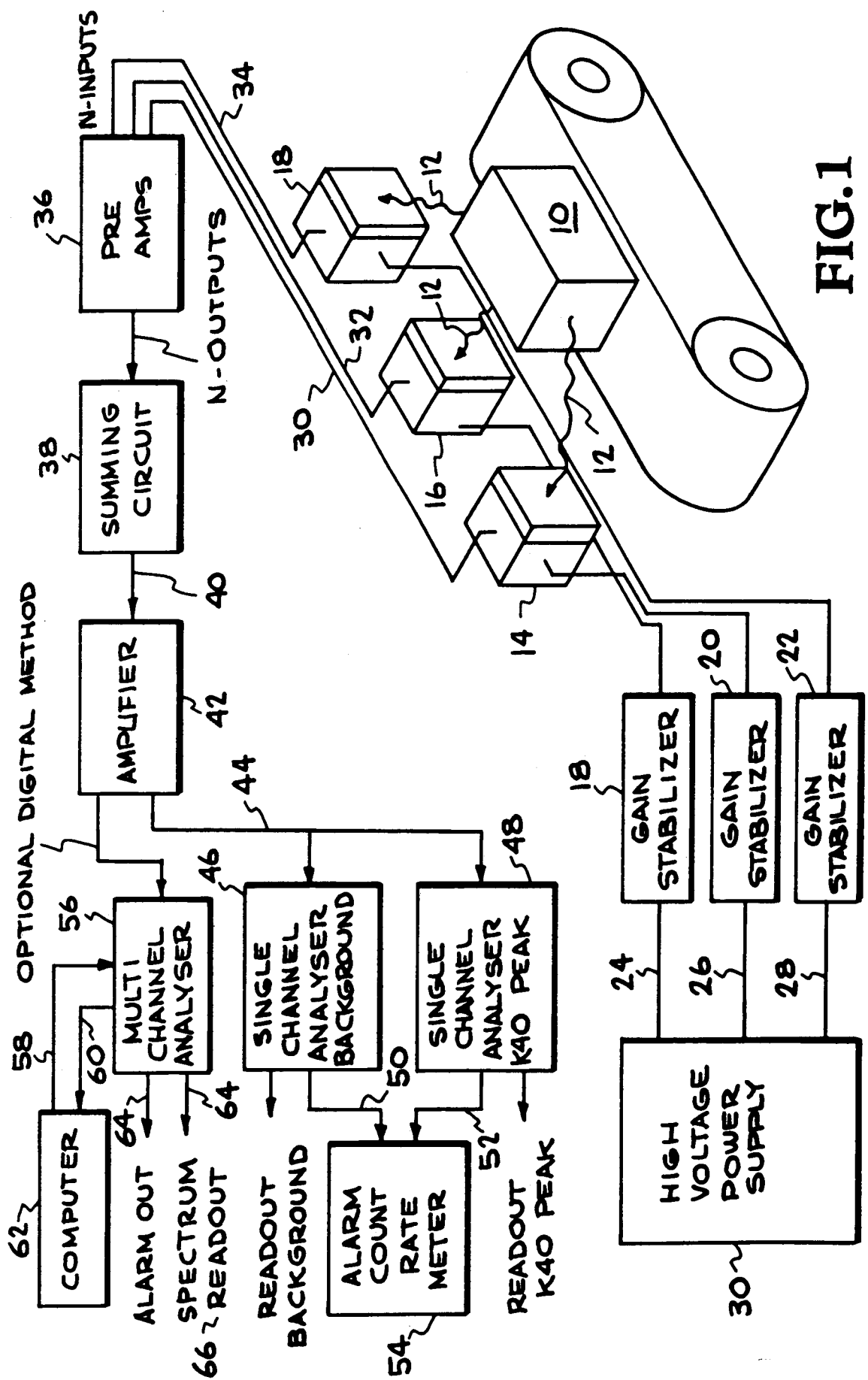
FIG. 1 is in part a perspective view illustrating the process of the invention, and in part a schematic block diagram illustrating apparatus used in the process of the invention.

In FIG. 1, there is shown a schematic diagram of the apparatus for carrying out the process of this invention. In this process, a piece of luggage or sample 10 containing a quantity of marijuana is positioned at a particular location. Gamma radiation [K40] 12 emanating from the marijuana in the luggage 10 is read by photomultiplier-sodium iodide detectors 14, 16 and 18. Although only three detectors are shown in FIG. 1, any number can be used. Generally speaking, the more detectors which are used, more accurate readings and, or, shorter count times will be obtained. Practically speaking, however, there is a limit on the number of detectors which can be positioned at any one location. Each of the photomultiplier-sodium iodide detectors 14, 16 and 18 are parallel connected by means of thermistor, resistor circuit 19, 20 and 22 through leads 24, 26 and 28 to a high voltage power supply 30 which serves to stablize the gain of each photomultipler tube 14, 16 or 18. Signals from the detectors 14, 16 and 18 are passed through leads 31, 32 and 34 to a preamp 36, and from the preamp 36 through lead to a summing circuit (or mixer) 38. From the summing circuit 38, a signal is sent through lead 40 to an amplifier 42 and a signal from the amplifier 42 is sent through lead 44 to a first single channel analyzer 46 which analyzes the background gamma count in an energy region above the K40 energy peak and to a second single channel analyzer 48 which analyzes the peak K40 radiation count. As discussed later, analyzer 46 may not be necessary. Output signals from the background analyzer 46, and the peak analyzer 48, are transmitted through leads 50 and 52, respectively to an alarm circuit 54, which is calibrated so as to go off when the peak level readout is at a predetermined level in excess of the predetermined K40 background radiation count level.

The output from the single channel analyzers are in the form of voltage pulses that correspond to each detectable gamma ray in the region of interest. If this signal is sent to the alarm circuit, then the alarm circuit can be in the form of an up (peak analyzer), down (K40 region background analyzer) counter that is preset to alarm at a certain count in a set time period. This alarm method is called a "counter-timer".

Alternatively, the signal from the amplifier 42, can be transmitted by digital means through a multichannel analyzer 56 connected by appropriate leads 58, 60 to a computer 62 which is programmed to sound an alarm when the peak K40 radiation exceeds a predetermined background radiation by a predetermined amount. The combination of a computer and multi-channel analyzer is commercially available.

Obviously, alternative circuits to those set forth in FIG. 1 can be devised by a person skilled in the art. The essential components of the system include detectors to detect K40 radiation emananting from a source, i.e., a piece of luggage, with the detectors being connected by appropriate circuitry to an alarm or readout system which is triggered when the level of K40 radiation emanating from the sample exceeds the background radiation by a predetermined amount.

The alarm circuit 54 can also take the form of a "mean level system" by using the single channel analyzer pulse outputs to drive two count rate circuits. The count rate circuit outputs will be analog voltages whose levels are proportional to background and peak count rates. These count rate meters also have selectable time constants that determine how fast their outputs respond to a count-rate change. The desired time constants are set based on predetermined statistical considerations. The alarm is set to go off if the difference between the two signal levels reaches a predetermined amount.

In both the "mean level" and "counter-timer" configurations, the difference signal (64) is proportional to the amount of K40 present in the sample and can be output to an indicator or display (66) to indicate the amount of K40 (or marijuana) present.

Not shown is the gamma shielding around the assembly that will enhance the system sensitivity.

Figure 2:
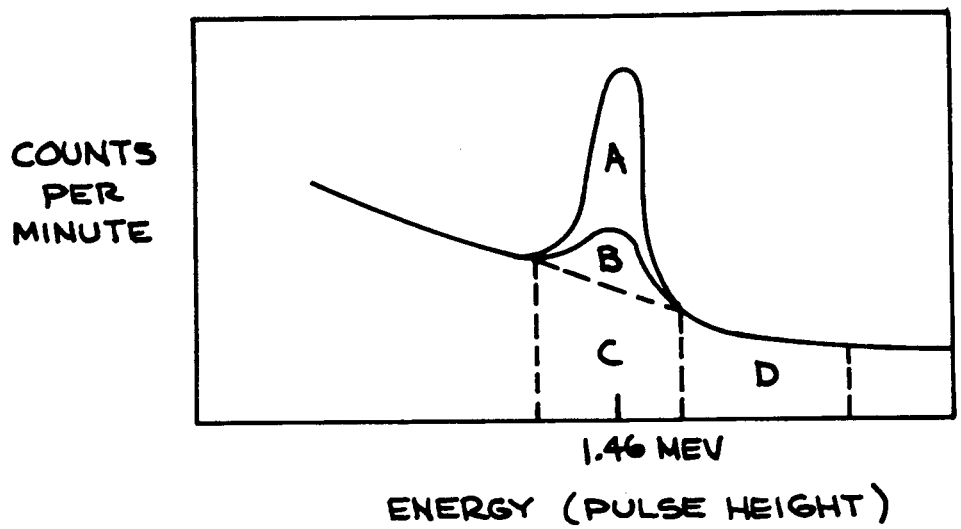
FIG. 2 is a graph of a typical pulse height spectrum in the 1.46 MeV region.

FIG. 2 represents a pulse height spectrum in the 1.46 MeV region. The peak region A (which includes B) represents K40 counts obtained from a sample containing some amount of K40 plus the counts due to background K40 (represented by Region B). Single channel analyzer (SCA) 48 registers the total counts contained in A+C (or B+C). The Count C is due to higher energy gamma ray's partial absorption in the detector. Since A and B represent completely absorbed K40 gamma, the Area C must be subtracted from this SCA 48 count to obtain A:

$SCA$ 48 counts $= A + C$ $A = SCA$ 48 counts $- C$

Count C cannot be obtained directly. There are two methods using SCA circuits that can be used, however, to obtain Count A. The first method assumes that the shape of the curve under and immediately adjacent of the K40 peak remains the same for the K40 count rate range expected. If that is true, then Area C is proportional to Area D, where Area D is counted with SCA 46.

$C = (K) \times (D)$

K is a constant
Therefore, $$A = SCA\ 48\ \text{count} - (K \times SCA\ 46\ \text{count})$$
$$= A + C - (K \times D) = A + C - C$$

The count rate represented by Area B will have been previously determined by long counts and will sound the alarm when A>B by a predetermined amount as discussed later. The drawback with using two SCA circuits is that, because of the short count times expected and low count rates from SCA 46 and 48, the counting statistics will be degraded when we subtract because $$\sigma_A = \sqrt{\sigma_A + C^2 + K\ \sigma_D^2}$$

where $\sigma$ represents the standard deviation of counts.

If, however, it is assumed that not only does the shape of the curve in and around the region of interest stay the same, but the count C is reasonably constant, then a second method can be used to obtain the Count A. If these assumptions are correct, then Area C count rate can be determined along with Area B by a long count previously obtained (perhaps once a day to check the equipment). If Area C is thus determined, the $\sigma$ will be small and SCA 46 is not needed. In this case:

$$\sigma = \sqrt{\sigma_A + C^2 + \sigma_{C^2}}$$

where $\sigma_A + C^2 >> \sigma_{C^2}$
therefore $^a A = {^a A} + C$

The continuum under the peak is due to higher energy gamma rays that are partially absorbed in the detector and should be fairly independent of the sample or luggage since it should not contain an appreciable amount of any higher energy gamma emitters. The method used will have to be determined and will be a function of the detectors and environmental conditions for a particular setup.

The later calculations assume that the second method is used and that SCA 46 is not necessary.

In the process of this invention, for gamma counting purposes, 1.46 MeV gamma ray energy is ideal for two reasons: first, with consideration of the energy resolution capabilities of sodium iodide or CsI scintillation crystal-photomultiplier gamma ray detectors, there are no significant interfering peaks from naturally occurring radionuclides. There may be man-made radionuclides that could interfere (especially cobalt 60 with gamma peaks at 1.17 and 1.36 MeV), but these would unlikely be present in sufficient quantities to be a problem. In fact, a side benefit of the system of this invention is the detection of such hazardous and most likely contraband radioactive materials.

Secondly, a 1.46 MeV gamma ray is quite penetrating and must travel through 104 meters of air, 1.2 cm of lead, or 5.1 cm of aluminum to have a 50 percent probability of undergoing an energy attenuating reaction. Since the only means of being certain that the counters 14, 16 and 18 are counting gamma rays from K40 is by complete absorption of the characteristic 1.46 MeV gamma ray in a detector, any energy reduction of the gamma ray due to an attenuating reaction before the gamma reaches the detector would make it useless for K40 identification or quantifying purposes. Practically speaking, because of the high energy of K40 gamma rays we can neglect the attenuating effect of packaging or air, and the potential counter measure of lead shielding is impractical because the weight needed would be a large (10 to 100) multiple of the weight of the plant substance. For example, it can be shown that if lead is used to shield 1000 gm of marijuana to the equivalent gamma flux of 100 gm at least 34,800 grams (77 pounds) of lead would be required. Also, for example, an aluminum suitcase with a wall thickness of 0.2 centimeters would only attenuate about 2.5 percent of the 1.46 MeV gamma rays, and an air distance of 1 meter results in an attenuation of only 0.6 percent.

While the process described can be applied to numerous situations, i.e., truck stops, weigh stations, ship-to-ship, and the like, the most useful situation is the inspection of luggage at airports, or similar situations, because the system variables and geometry can be more easily controlled and predicted.

Further, while the process can be used to detect any illegal plant substance which gives off potassium 40 gamma rays, it is particularly suitable for the detection of marijuana. Marijuana contains a higher level of potassium than many other materials that would be present in the described environment. Consequently, the amount of potassium 40 gamma rays given off is correspondingly high. Therefore, the detection of marijuana will be emphasized herein.

The emission rate of gamma rays is a random process and subject to statistical considerations, therefore, the minimum detectable limits are not absolute, and levels of marijuana (K40) below these limits can be detected, but with a lower probability of detection. For example, assuming typical system parameters, if a system has a detection confidence level of 97 percent at 270 grams of marijuana, the system would have a 50 percent detection confidence level at 100 grams and a 24 percent detection confidence level at 50 grams. Stated another way, for the system defined there is a 97 percent chance of being apprehended with 270 grams of marijuana, a 50 percent chance with 100 grams, and a 24 percent chance at 50 grams. The confidence level, which is defined at the lower detection limit, is arbitrarily established by those individuals doing the detecting.

Theoretically, any lower detection limit can be chosen and an appropriate system designed. However, there are practical limitations due to the following considerations. First, it should be recognized that nearly all materials contain some potassium, even if their concentration are much smaller than marijuana. Table I below lists some common materials and their K40 concentrations. If, for example, the lower detection limit of the system is set to 1 gram so as to be able to detect one marijuana cigarette, then it is also possible to trigger an alarm for a single pack of tobacco cigarettes or about 11 grams of bananas. If the lower limit is set at 200 grams of marijuana, the equivalent amount of tobacco (assuming tobacco has a concentration of 10 pCi/gram of K40) would be about 4 cartons of cigarettes or about 1.2 pounds of bananas, both of which would be highly unlikely luggage contents. Therefore, the practical lower limit to design a system around is really concerned with the question of how many suitcases or packages that have triggered an alarm one is willing to physically inspect to make sure that the lower detection limit of marijuana is not missed.

TABLE I

| MATERIAL | APPROXIMATE K40 CONCENTRATION (pCi/gram) | EQUIVALENT WEIGHT TO CONTAIN THE SAME AMOUNT OF K40 AS IN 200 GRAMS OF MARIJUANA (GRAMS) |
|---|---|---|
| Marijuana | 35 to 50 | 200 |
| Milk (whole) | 1.29 | 6600 |
| Soil | 5 to 50 | 1700 to 170 |
| Aluminum | 0.03 | 283333 |
| Steel | 0.04 | 212500 |
| Pyrex | 1.7 | 5000 |
| Rubber | 0.8 | 10625 |
| Cement (Portland) | 2 | 4250 |
| Plastic | .01 | 850000 |
| Hay | 20 | 425 |
| Banana | 3.2 | 2666 |
| Bread | 0.9 | 9883 |
| Cocoa, Dried Powder | 13 | 650 |
| Beef, Lean | 2.8 | 3000 |
| Cotton, Pure | 4.1 | 1710 |

Any increase in desired system sensitivity must be paid for in either system cost or time spent counting each piece of luggage. The number of detectors required (assuming the count time remained the same and the background count is directly proportional to the number of detectors) to lower the detection limits from W1 to W2 can be expressed as follows:

$$\frac{\text{number of detectors for } W2}{\text{number of detectors for } W1} = \frac{W1^2}{W2^2}$$

Thus, to lower the detection limits from 200 grams to 1 gram, the number of detectors would have to be increased by 40,000, clearly an impractical situation.

The equation set forth below assumes a normal distribution of the probability as a function of the number of gammas counted for a set count time. The normal distribution is a good approximation for total counts above about 15, but deviates from the more correct poisson distribution as the total count gets lower. Also, the normal distribution is a continuous function and, therefore, results are obtained that involve fractional counts. When the counter-timer or digital scheme is used, the equipment can only register integer counts; therefore, the required count times, as calculated from the normal distribution, must be adjusted to obtain the nearest integer count. For example, if a calculated count time of 5 seconds results in 2.5 calculated counts for the desired detection probabilities, the actual count time would have to be adjusted to 4 to 6 seconds to obtain 2 or 3 counts respectively, and the actual detection probability would be different than the designed probability. However, the numbers obtained from the normal distribution are close enough for illustrative purposes.

The minimum detectable limit varies as the square of the source to detector spacing. Because the variations of placement of the drug in the luggage will most likely introduce a significant uncertainty in the actual detector to source spacing for one detector, it is possible to have a large variation in the actual sensitivity of the system in the form of minimum detectable weight of the drug. However, if several detectors are employed around the expected counting position of the luggage and physically limit the minimum distance possible between any one detector and the drug, the variation and system sensitivity can be reduced.

The optimum placement of the detectors and counting geometry for a particular situation can be determined by empirical means and/or knowledge of the geometric variations expected.

The time needed to count each piece of luggage is dependent on the system parameters and lower detection limits desired. The number of detectors needed (or total detector volume) can be calculated if the maximum counting time available and desired minimum detectable limits and probabilities are specified and a realistic background count is known or assumed. If a maximum number of detectors is specified and the maximum available count time is known, the resulting minimum detection limits can be calculated. In either case, the amount of time available for counting each piece of luggage must be specified and can be obtained from a knowledge of the operations research parameters of the particular system location.

Basically, there are two methods of electronically implementing a fieldable system: a mean level system and a counter-timer system. For both systems, it is necessary, through long counts, to establish a background count rate in the K40 gamma energy region for the actual environment conditions. This background rate must be periodically checked to determine if it has changed. The purpose of both systems is the same: to trigger an alarm if it is P2x×100 percent certain that the gamma count rate in the 1.46 MeV region is due to sources other than statistical fluctuations in the background count rate, where $P_2$ is set by design, typically 0.97. Because there is only a certain time (Tm seconds) available for each piece of luggage, the system is designed so that, at T=Tm, the amount of marijuana (K40) that is determined to be the minimum detectable quantity (Wm), will trigger the alarm in P3m×100 percent of the cases when it is present. If the average background count rate is constant, P2 will remain constant. However, P3 is a function of the amount of K40 in the luggage, and by convenient definition, the minimum detectable quantity (Wm grams) is the amount of marijuana at its minimum K40 concentration (30 piC/gram) that will cause P3 to be 0.5 (50 percent, P3m) assuming a normal probability distribution.

With the single channel analyzer circuit the detector pulses are routed to a single channel analyzer that produces a constant height pulse for each detector pulse in the 1.46 MeV region. The counter counts these pulses for Tm time and is reset for each piece of luggage. The alarm level in counts is set at kx (standard deviation of K40 background counts for counting period $T_m$), where the value of k is a function of P2, and the actual number of counts accumulated is compared to this alarm level at the end of the counting time Tm. If k=1.88, then P2=0.97, which means that the total count will reach or exceed this amount in only (1-0.97)×100 percent=3 percent of the cases where there is no other gamma source present other than background. A count due to an amount Wm grams of marijuana plus background will (on the average) be equal to the alarm level. Because of the random nature of radioactive decay, it can be expected that in half the cases the total count due to background plus Wm will be at or below the alarm level, therefore, P3m=0.5.

For both systems, the count rate out of the single channel analyzer due to W grams of material alone (no background) and assuming a point source can be expressed as:

$$CT = \frac{323.8 \times 10^{-6}(A\ C\ W\ E\ \#)}{R^2}$$

Where:
 CT=counts per second
 A=front area of each detector (cm$^2$)
 C=concentration of K40 in sample (piC K40/gram)
 W=mass of sample material (grams)
 E=fractional efficiency of detector for parallel beam of gammas at 1.46 MeV (counts/gamma incident to front surface of detector)
 #=number of detectors
 R=distance from sample to detector front surface (cm)

The foregoing assumes that mean the alarm level is set at 1.88×(standard deviation of counting system, K40 background) above the true background count rate.

This corresponds to a 97 percent confidence level that the alarm is not due to the background count rate.

The expression for the approximate value of the needed count time is:

$$Tm = \frac{k_1^2\ r_1}{(CT)^2}\ \#$$

where
 Tm=count time in seconds
 $r_1$=Background count in K40 region (SCA 48) for each detector
 #=Number of detectors
 CT=Counts per second in K40 peak of detector from luggage or sample as expressed in page 31
 $k_1$=Multiplier factor that determines $P_1$ (the probability that an alarm is not false)
  if $K_1$=1.88, $P_1$=0.97 (97%)
  if $K_1$=2.66, $P_1 \geq 0.997$ The value for $k_1$ of 2.66 corresponds to doubling the count time for that calculated for $K_1$=1.88. This means that if an alarm is sounded, the count could be continued for a second count and the certainty of not obtaining a false alarm would increase from 97% to 99.7%. Therefore, it would be more certain that the alarm was real if it again sounded at the end of the second count time.

For a prototype system consisting of eight 4-inch by 4-inch NaI(t1) detectors at a distance of 25 centimeters, with a concentration of K40 of 30 pCi/gram marijuana, using a mean counting system (count rate readout) with a 97 percent certainty of real alarm, it would require about 9 seconds for a 200 gram lower detection limit. For a count time of 3 seconds, the lower detection limit would be about 321 grams. This assumes a background rate of 7.2 K40 counts per minute for each detector.

The individual components of the apparatus used in carrying out the process of this invention are commerically available. For example, the photomultiplier-NaI detectors 14, 16 and 18 can be purchased from the EG&G Corporation under the designation Ortec 905-4.

The thermistors 18, 20 and 22 are sold by the many vendors, and the high voltage power supply 30 is sold by the EG&G Corporation under the trade designation Ortec 556.

The preamp 36 is sold by the EG&G Corporation under the trade designation Ortec 113, and the summing circuit 38 by EG&G under the designation Ortec 590A.

The single channel analyzers 46 and 48 can be purchased from EG&G Corporation under the designation Ortec 550, and the alarm circuit 54 under the designation Ortec 541.

The multichannel analyzer 56 and associated computer 62 is sold by EG&G Corporation under the trade designation Ortec "Ace".

Apparatus performing the same function as the above referenced units can be used instead of the ones specifically mentioned.

This invention will be more fully understood by reference to the following examples, which are intended to illustrate the process and apparatus of the invention, but not be limiting thereof.

In the examples to follow, a calculation of system performance using $3'' \times 3''$ and $4'' \times 4''$ NaI(TL) scintillation detectors is made. Although not the optimum detector for our purposes, the literature contains a significant amount of data for these detectors. The following summary of detector parameters and background count rates for a carefully shielded system are used for all examples and curves.

$3'' \times 3''$ Detector

A = 45.61 cm 2
E = 0.25 counts/gamma (1.46 MeV)
r1 = 0.10 counts/second = background count rate in K40 region from detectors $4'' \times 4''$ Detector A = 81.07 cm 2
E = 0.33 counts/gamma (1.46 MeV)
r1 = 0.12 counts/second = background count rate in K40 region from detectors
A sample to detector distance of 25 cm is used.

EXAMPLE 1

The probability distribution and alarm probability for eight 4" by 4" NaI(TL) detectors for a count time of 3 seconds is determined.

Figure 4:
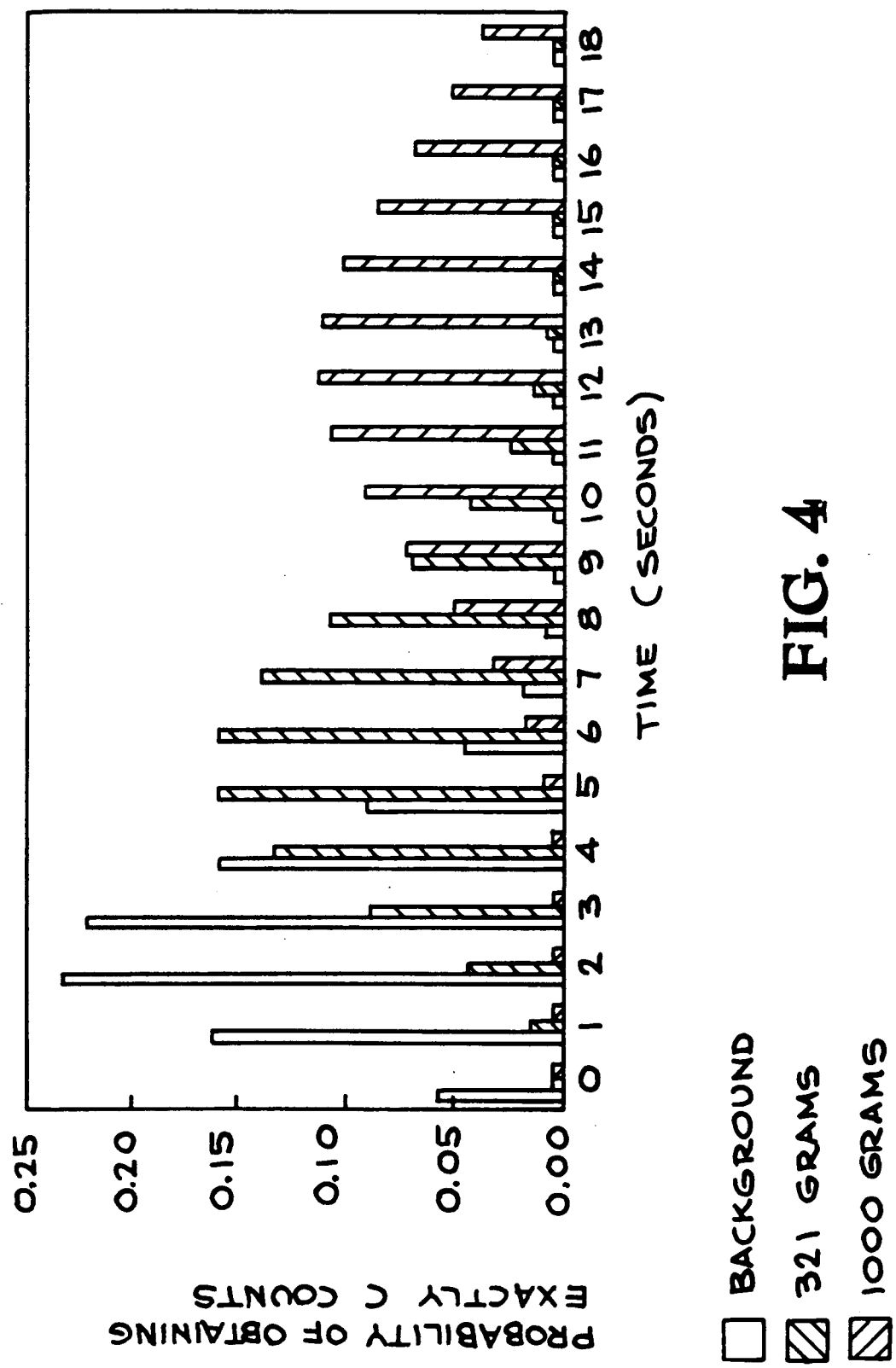
FIG. 4 is a graph showing the probability distribution for eight 4"×4" NaI(TL) detectors for a count time of 3 seconds.
Figure 5:
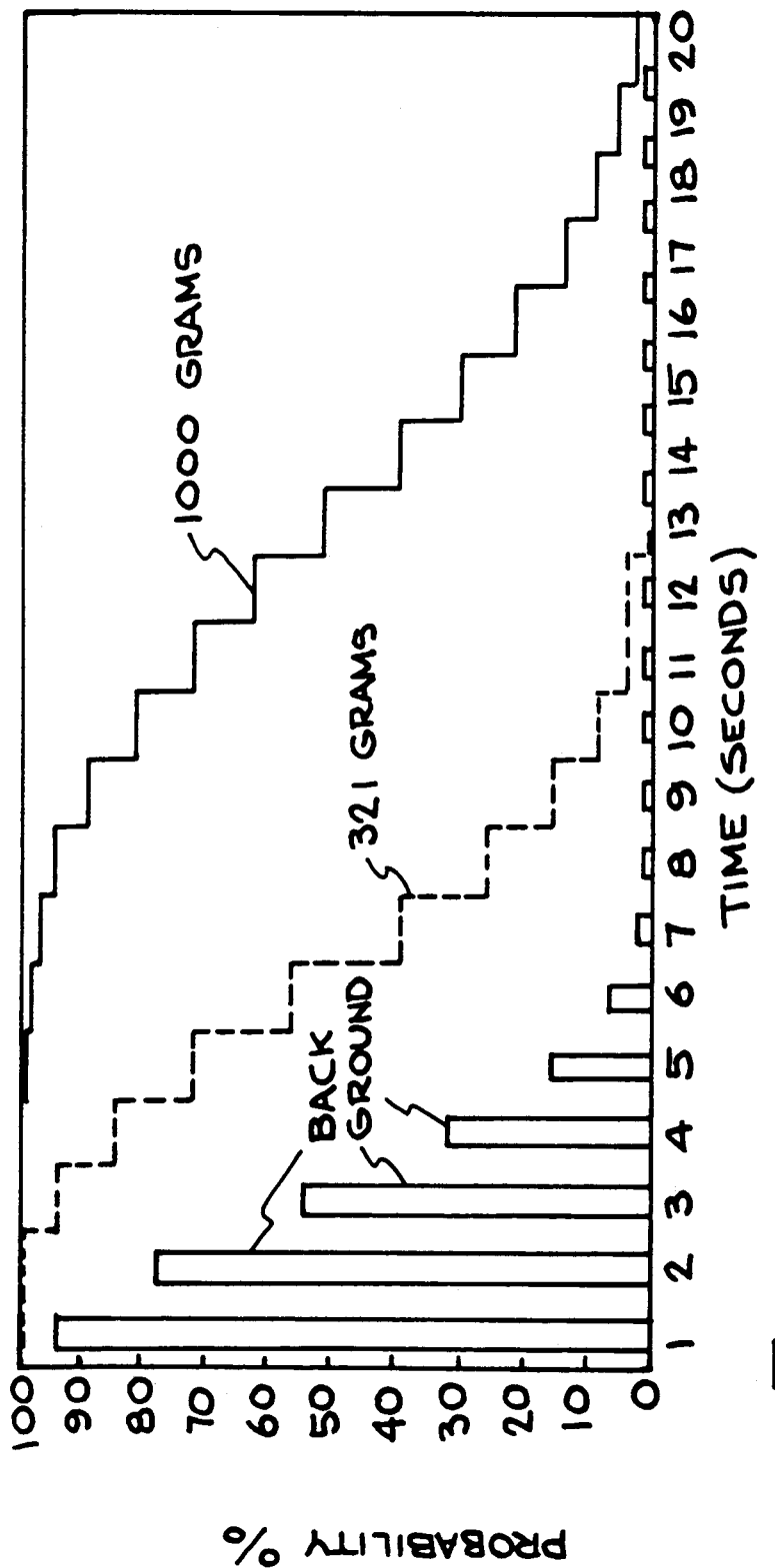
FIG. 5 is a graph showing the alarm probability for eight 4"×4" NaI(TL) detectors for a count time of 3 seconds.

As seen in FIGS. 4 and 5, the normal distribution predicts an alarm level of about 6 counts for 3 seconds count time. This corresponds to a Wm of about 3221 grams of marijuana.

Figure 3:
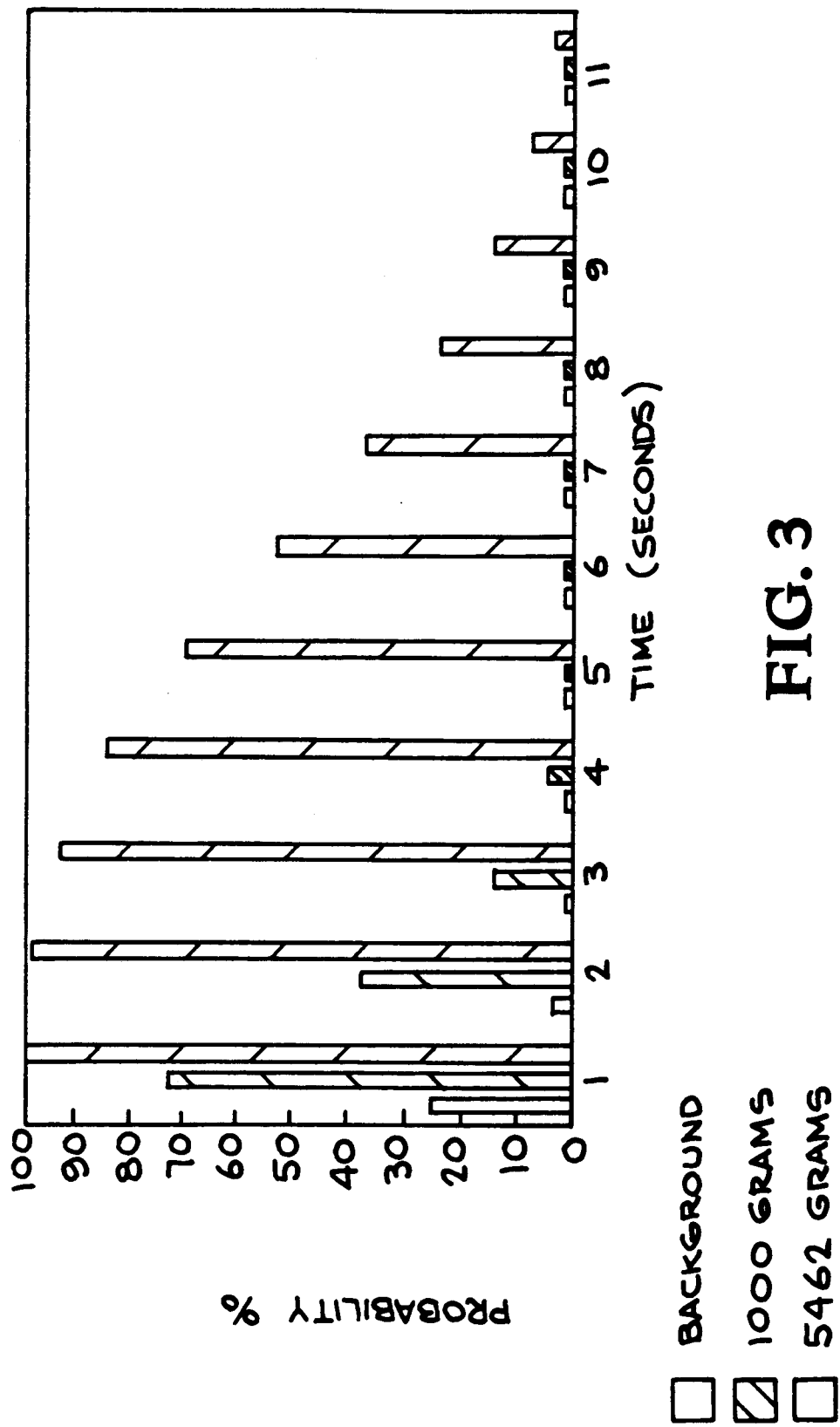
FIG. 3 is a graph showing the alarm probability for eight 4"×4" NaI(TL) detectors for a count time of 0.3 seconds.

The values for the same detectors with a count time of 0.3 seconds is shown in FIG. 3. If the alarm level is set at 2 counts, there would be about a 3% chance of a false alarm, a 38% chance of alarm at 1000 grams, and a 98% chance of alarm at 5462 grams.

EXAMPLE 2

The relationship between the amount of marijuana (Wm) and the needed count time for P2=97% and P3=50%, for (a) 8 $3'' \times 3''$ detectors, (b) 8 $4'' \times 4''$ detectors, and (c) 3 16" detectors, is determined.

The 16" detector calculations are made using data supplied by the Bircon Corporation, with the peak background count rate doubled, and E=0.44 counts/gamma.

Figure 6:
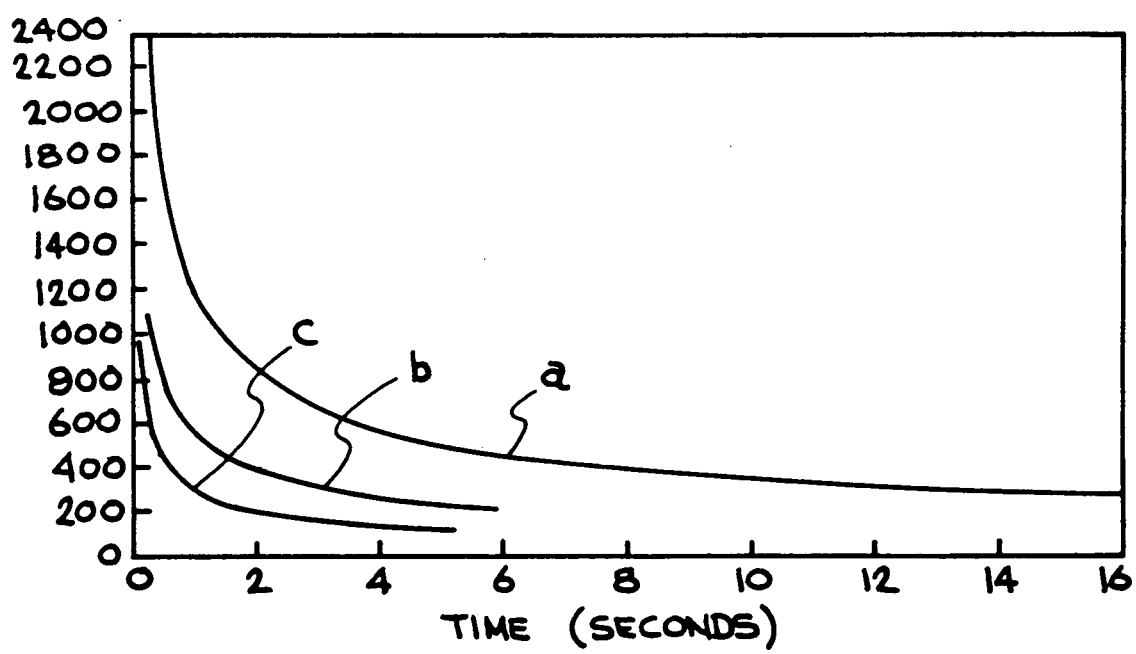
FIG. 6 is a graph showing the relationship between the amount of marijuana and needed count time for various gamma ray detector systems at various confidence levels.

A graph showing the results of these calculations is shown in FIG. 6. 5 The foregoing description of preferred embodiments of the invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention in various embodiments and with various modifications as are suited to the particular use contemplated. It is intended that the scope of the invention be defined by the claims appended hereto.

I claim:

1. A process for detecting the presence of plant substances in a particular environment which comprises the steps of:
    (a) measuring the background K40 gamma ray radiation level in a particular environment with a 1.46 MeV gamma ray counter system;
    (b) measuring the amount of K40 gamma ray radiation emanating from a package being passed through said environment with said counter; and
    (c) signaling the presence of plant substances by generating an alarm signal when the total K40 gamma ray radiation reaches a predetermined level over and above the background level.

2. The process of claim 1 wherein said plant substance is marijuana.

3. The process of claim 1 wherein a plurality of 1.46 MeV gamma ray radiation counters are positioned at several points in said specific environment.

4. A process of claim 1 wherein the signal, which is generated when the total K40 gamma ray radiation reaches a predetermined level over and above the background level, is generated at a set confidence level.

5. A process of claim 2 wherein the 1.46 MeV gamma ray radiation counter system is calibrated so that the minimum level of marijuana detected is that amount which will cause an alarm in the desired percentage of cases.

6. The process of claim 1 wherein said package is located at a specific point within said environment.

7. The process of claim 1 wherein said alarm signal is an audible noise.

8. The process of claim 1 wherein said alarm signal is a light.

9. A system for detecting the presence of plant substances in a particular environment comprising in combination:
    a. means for detecting and counting the amount of K40 radiation emanating from a particular environment and generating a signal in response thereto.
    b. means for amplifying said signal,
    c. means for summing said signal,
    d. means for further amplifying said signal, and
    e. means for signaling the presence of plant substances comprising means for generating an alarm when the value of said signal reaches a predetermined level over and above a predetermined base level.

10. The system of claim 9 wherein (a) is a photomultiplier NaI detector and counter for K40 gamma rays.

11. The system of claim 9 wherein (b) is a preamplifier.

12. The system of claim 9 wherein (c) is a summing circuit.

13. The system of claim 9 wherein (d) is a signal amplifier.

14. The system of claim 9 wherein (e) comprises a first single channel analyzer for determining background level of radiation in the region around the peak energy at 1.46 MeV, a second single channel analyzer for analyzing peak K40 radiation, both being connected in parallel to an alarm circuit.

15. The system of claim 9 which optionally includes a multichannel analyzer connected in series with (d), and also to a computer, and which generates an alarm when the K40 radiation level emanating from said source reaches a predetermined level.

16. The system of claim 9 wherein when more than one photomultiplier NaI detector and counter is used, each is electronically connected to the other by means which stabilizes the gain of each photomultiplier tube.

17. The process of claim 1 wherein the signal generated when the total K40 gamma ray radiation reaches a predetermined level over the background level is used to display the quantitative amount of K40 in the package.

* * * * *